United States Patent [19]

Aoki

[11] Patent Number: 5,701,877
[45] Date of Patent: Dec. 30, 1997

[54] HEATER CONTROLLER FOR AN AIR-FUEL RATIO SENSOR

[75] Inventor: Keiichiro Aoki, Susono, Japan

[73] Assignee: Toyota Jidosha Kabushiki Kaisha, Aichi, Japan

[21] Appl. No.: 736,818

[22] Filed: Oct. 25, 1996

[30] Foreign Application Priority Data

Dec. 6, 1995 [JP] Japan ................... 7-318133

[51] Int. Cl.$^6$ ............... F02D 41/00; F02M 23/00; F02M 25/00
[52] U.S. Cl. .................................................. 123/697
[58] Field of Search ........................ 123/697, 489; 204/425, 420, 424, 406, 15

[56] References Cited

U.S. PATENT DOCUMENTS

| | | | |
|---|---|---|---|
| 4,694,809 | 9/1987 | Nakano et al. | 123/489 |
| 4,708,777 | 11/1987 | Kuraoka | 204/1 T |
| 4,938,196 | 7/1990 | Hoshi et al. | 123/697 |
| 5,111,792 | 5/1992 | Nagai et al. | 123/697 |
| 5,148,795 | 9/1992 | Nagai et al. | 123/697 |
| 5,353,775 | 10/1994 | Yamashita et al. | 123/686 |

FOREIGN PATENT DOCUMENTS

| | | | |
|---|---|---|---|
| A-38 42 287 | 8/1989 | Germany | 123/697 |
| A-41 06 308 | 9/1992 | Germany | 123/697 |
| A-1-158335 | 6/1989 | Japan . | |
| A-2 273 571 | 6/1994 | United Kingdom | 123/697 |
| WO 91/09219 | 6/1991 | WIPO | 123/697 |

*Primary Examiner*—Raymond A. Nelli
*Attorney, Agent, or Firm*—Oliff & Berridge

[57] ABSTRACT

This invention provides a heater controller applied to an air-fuel ratio sensor to prevent a temperature of the sensor excessively rising or the heater installed in the sensor breaking down, when a failed sensor is replaced with a new sensor without clearing a memory which stores a resistance of the heater of the failed sensor. A resistance of the heater for heating the sensor is calculated, and is stored as a stored resistance in a back up memory. When a failed sensor is replaced with a new sensor having a lower resistance than that of the heater installed in the failed sensor without clearing the memory, an electric power supplied to the heater is increased in accordance with a current resistance of the new heater and the stored resistance of the failed heater. However, the increased electric power is limited within a interval determined by an engine operating condition.

18 Claims, 12 Drawing Sheets

| THWs | 20 | 50 | 80 |
|------|-----|-----|-----|
| Tpg  | 100 | 60  | 10  |

| Qsum | 20000 | 50000 | 80000 |
|------|-------|-------|-------|
| Tpg  | 100   | 60    | 10    |

HEATER CONTROLLER FOR AN AIR-FUEL RATIO SENSOR

BACKGROUND OF THE INVENTION

1. Field of the Invention

This invention relates to a heater controller for an air-fuel ratio sensor, and more especially to a heater controller for controlling electric power supplied to a heater for heating an air-fuel ratio sensor to prevent the temperature of the sensor rising excessively when the heater with a high resistance value, which has been stored in a memory is replaced another heater with a low resistance value.

2. Description of the Related Art

It is widely known to control an air-fuel ratio of air-fuel mixture supplied into a cylinder of an engine at a fixed target air-fuel ratio (for example, the stoichiometric air-fuel ratio) by correcting a basic fuel amount in accordance with an oxygen amount contained in exhaust gas in order to improve the nature of the exhaust gas emission, the fuel cost and the vehicle drivability.

To achieve the above-mentioned air-fuel ratio control, it is indispensable to detect the amount of oxygen contained in the exhaust gas. It is also necessary to keep the temperature of an air-fuel ratio sensor at a fixed temperature (for example, 650° C.) by heating the sensor with a heater, because the output voltage of the sensor is influenced not only by the oxygen concentration but also by the temperature of the sensor.

Therefore, the temperature of the sensor is maintained at the fixed temperature by controlling the calorific heat generated by a heater installed in the sensor by controlling the electric power supplied to the heater. Further, the electric power supplied to the heater is grater during a warming up of the sensor after a start of the engine than during a normal operating condition so that the sensor becomes active as soon as possible after the starting of the engine.

Because an excessive temperature rise, or break-down of the heater, may occur when the electric power is increased, it is necessary to limit an electric power supplied to the heater so that the resistance of the heater does not exceed a predetermined fixed resistance corresponding to an allowable upper limit temperature under which the break-down of the heater does not occur. The resistance of the heater, however, has an allowable dispersion.

FIG. 2 shows characteristic curves of heaters, and the abscissa denotes a resistance of a heater and the ordinate denotes a temperature of a heater. This graph shows that a resistance of a heater can be distributed between an allowable maximum resistance and an allowable minimum resistance, and the center thereof denotes the resistance of a standard heater.

Therefore, if an electric power supplied to the heater is limited so that the resistance of the standard heater does not exceed the predetermined fixed resistance Ra corresponding to the allowable upper limit temperature Ta, the activity of a sensor having a heater with a high resistance (for example, a heater with the allowable maximum resistance) may be delayed because an electric power supplied to the heater is limited so that the temperature of the heater does not exceed Tb which is lower than Ta. On the other hand, an excessive temperature rise may occur when a sensor having a heater with a low resistance (for example, a heater with the allowable minimum resistance) is used.

To solve the above described problem, a heater controller which controls the electric power supplied to the heater in accordance with a current heater resistance and a stored heater resistance which was stored as the stored resistance in a battery backup memory when the temperature of a heater is roughly stable during a warm up of an air-fuel ratio sensor after a start of an engine, has already been proposed (See, for example, Japanese Unexamined Patent Publication 1-158335).

According to the above-mentioned heater controller, however, when an air-fuel ratio sensor having a heater with any resistance fails after its resistance is stored and it is replaced with a new air-fuel ratio sensor having a heater with lower resistance than the failed sensor without the battery backup memory being reset, that is, without the battery backup memory being disconnected from a battery), it is unavoidable that a temperature of the new heater excessively rises to cause break-down.

SUMMARY OF THE INVENTION

Accordingly, an object of this invention is to provide a heater controller able to prevent the temperature of the heater rising excessively or the heater break-down.

According to the aspect of this invention, there is provided a heater controller, for controlling an electric power supplied to a heater for heating an air-fuel ratio sensor which detects an air-fuel ratio of an internal combustion engine, comprising: an engine condition determining means for determining an operating condition of the engine; a resistance detecting means for detecting a resistance of the heater; a storing means for storing the resistance detected by said resistance detecting means as a stored resistance when it is determined that a temperature of the heater is stable based on the engine operating condition determined by said engine condition determining means; an electric power increasing means for increasing an electric power supplied to the heater in accordance with the current resistance detected by said resistance detecting means and the stored resistance stored in said storing means during a warm up of the sensor after a start of the engine; and a limiting means for limiting an interval for supplying the electric power increased by said electric power increasing means within a predetermined fixed interval so that a temperature of the heater does not exceed an allowable upper limit temperature regardless of the resistance of a heater.

According to this invention, the heater controller can prevent the temperature of the replaced heater excessively rising to cause breaking down, because the electric power is increased in accordance with the current resistance of the heater and the stored resistance and is supplied only within a predetermined interval so that a temperature of a heater does not exceed an allowable upper limit temperature regardless of a resistance of the heater.

BRIEF DESCRIPTION OF THE DRAWINGS

The present invention will be more clearly understood from the description set forth below with reference to the accompanying drawings; where.

DETAILED DESCRIPTION OF THE PREFERRED EMBODIMENT

Figure 1:
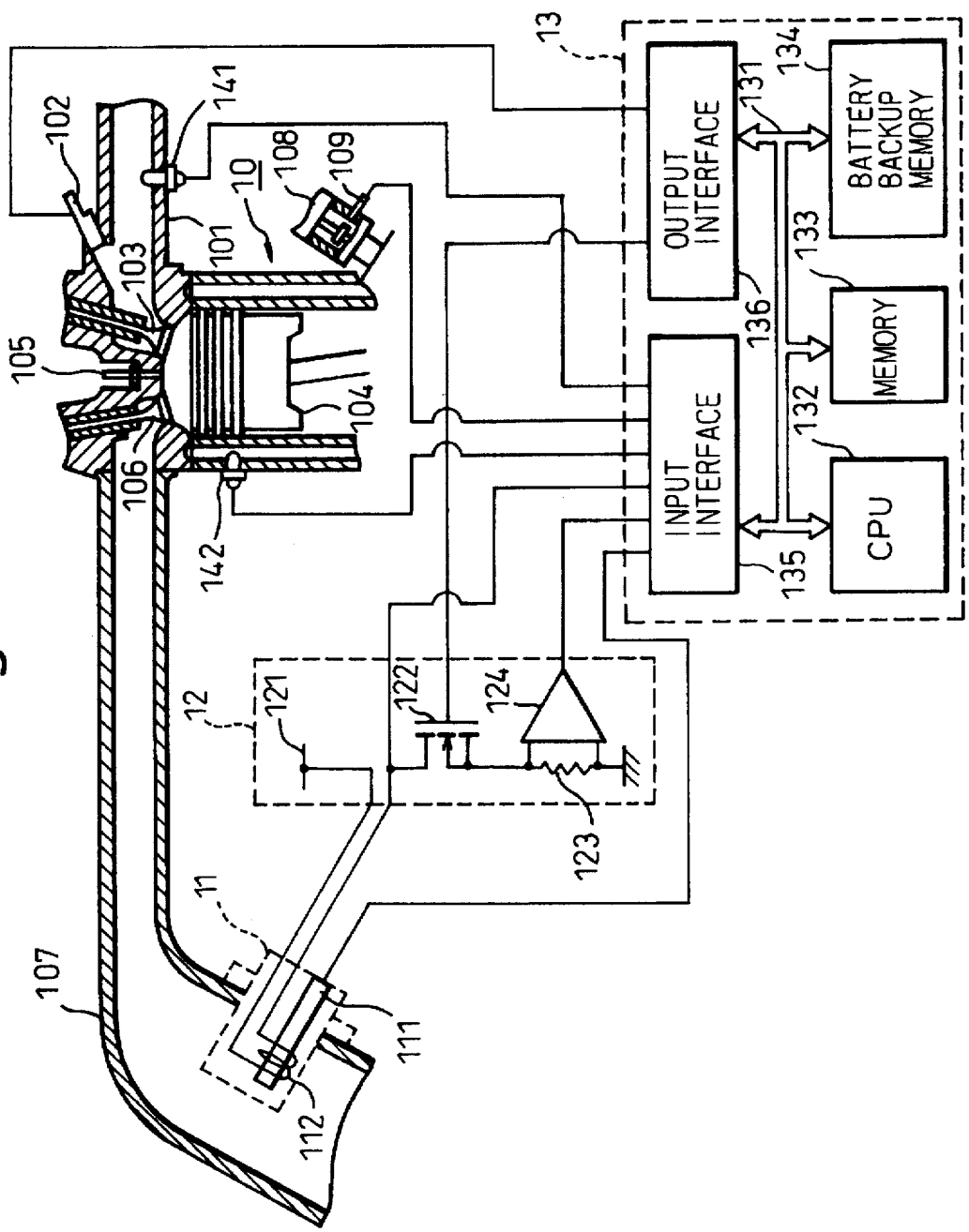
FIG. 1 is a block diagram of a preferred embodiment of a heater controller according to this invention.
Figure 2:
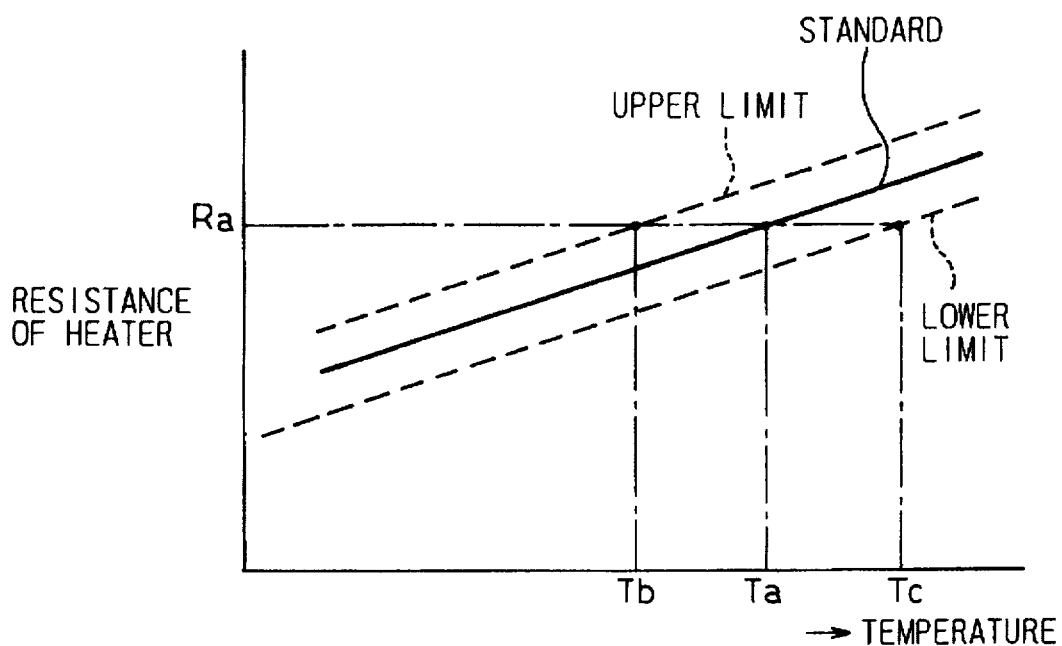
FIG. 2 is a characteristic curve of a heater of the sensor.

FIG. 1 shows a diagram of the preferred embodiment of a heater controller for an air-fuel ratio sensor according to the present invention, wherein a mixture composed of air supplied through an intake pipe 101 and fuel injected from an injector 102 is supplied to an internal combustion engine 10 through an intake valve 103.

The mixture is compressed by a piston 104, and the compressed mixture is ignited by an igniter 105 and then pushes the piston 104 down. Exhaust gas produced by the burning of the mixture is exhausted to an exhaust pipe 107 through an exhaust valve 106.

The engine speed of the engine 10 is detected by a speed detector 109 built into a distributor 108.

On the exhaust pipe 107, an air-fuel ratio sensor 11 is installed. The air-fuel ratio sensor 11 has a detecting element 111 which detects the oxygen concentration and a heater 112 which heats the detecting element 111.

The heater obtains electric power from a driving circuit 12 which is composed of an electric power source 121, a switching element 122, a resistor for measuring current 123, and a buffer amplifier 124.

The heater 112, the switching element 122, and the resistor 123 are connected in series between the electric power source 121 and an earth (the vehicle body). A current flowing through this series connection is detected by measuring a voltage across the resistor 123 for measuring current through the buffer amplifier 124.

A controller 13 is a microcomputer system which is composed of a bus 131, a CPU 132, a memory 133, a battery-backup memory 134, an input interface 135, and an output interface 136.

Note, data stored in the battery-backup memory 134 is not lost when a main switch of the automobile is turned off and further an ignition key is drawn out, as long as the battery-backup memory 134 is not removed from a battery (that is, as long as the memory is not cleared by removing the backup battery).

Not only the speed detector 109 and the detecting element 111 of the air-fuel ratio sensor 11, but also a vacuum sensor 141 installed on the intake pipe 101 and a coolant temperature sensor 142 are connected to the input interface 135.

A valve opening command for the injector 102 and an ON/OFF command for the switching element 122 are output from the output interface 136.

Figure 3:
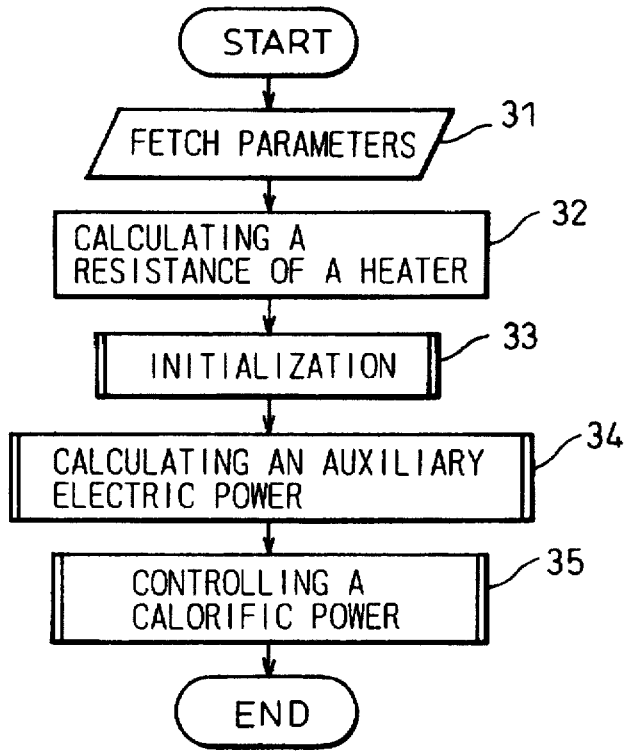
FIG. 3 is a flow chart of a first heater control routine.

FIG. 3 shows a flow chart of a first heater control routine executed in the controller 13. An engine speed Ne, an intake vacuum Pm, a coolant temperature THW, a voltage Vh supplied to the heater, and a current Ih flowing through the heater are fetched at step 31.

At step 32, a resistance Rh of the heater is calculated based on the voltage Vh supplied to the heater and the current Ih flowing through the heater by using a following equation.

$$Rh \leftarrow Vh/Ih$$

Then this routine is terminated after an initalizing routine, an auxiliary electric power calculating routine and a calorific power control routine are respectively executed at step 33, at step 34 and at step 35.

Figure 4:
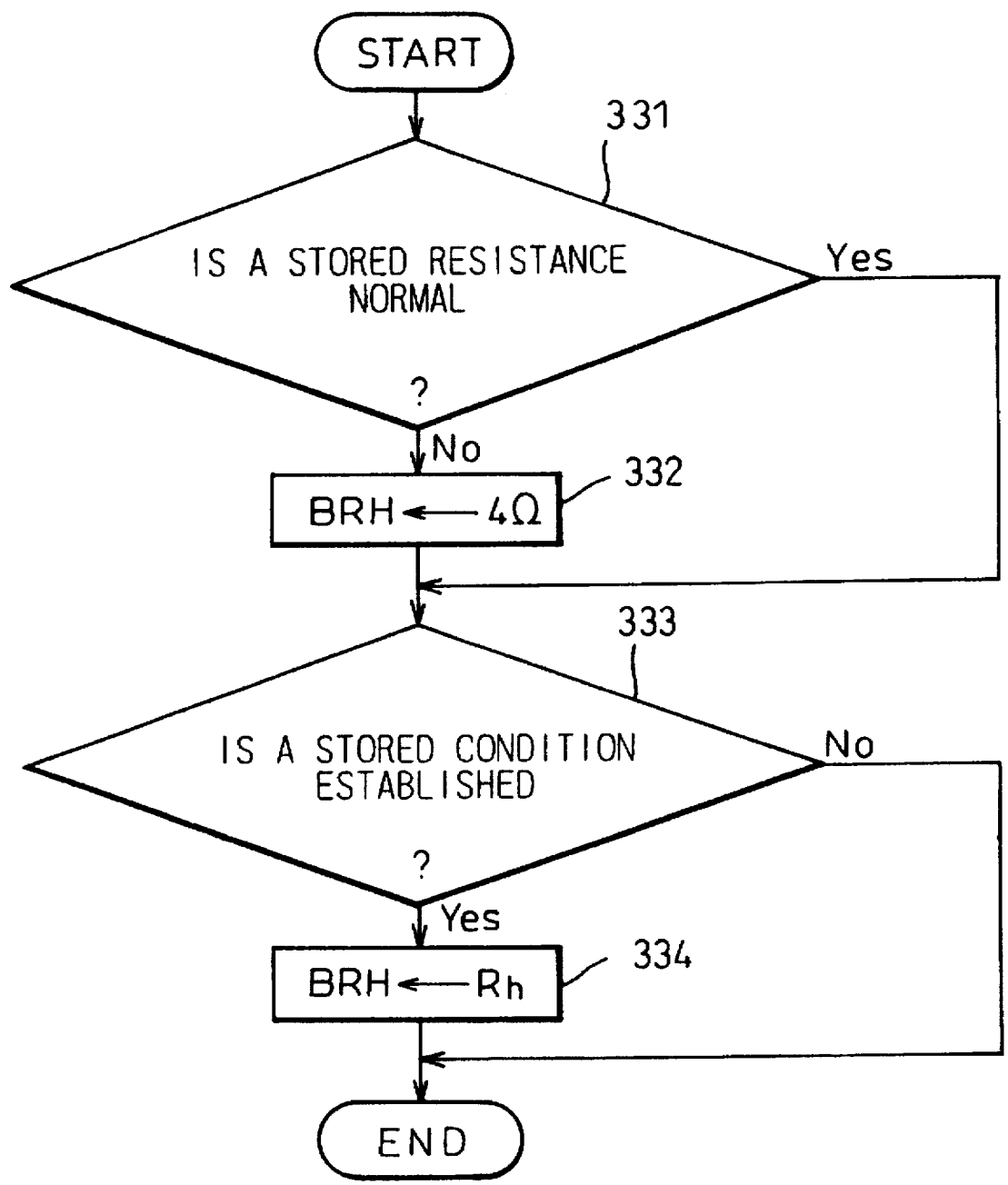
FIG. 4 is a flow chart of an initializing routine.

FIG. 4 is a detailed flow chart of the initializing routine executed at step 33, which determines whether or not a stored heater resistance stored in the battery backup memory 134 is normal at step 331.

The above-mentioned determination, for example, can be realized by storing not only the heater resistance but also its reciprocal at a storing stage and confirming that those two numbers are mutually in a reciprocal relationship when determining whether or not the stored resistance is normal.

When the determination at step 331 is negative, the control proceeds to step 333 after the stored resistance BRH is set to the predetermined standard value (for example, 4 ohms) at step 332. Note, when the determination at step 331 is affirmative, the control proceeds directly to step 333.

At step 333, it is determined whether or not a condition for storing a resistance of the heater is established.

The storing condition is established when a temperature of the heater is maintained at a fixed temperature and the operating condition of the automobile is stable. This condition can be confirmed by determining whether or not following three conditions are established.

(1) Whether or not an air-fuel ratio feedback control is being executed.

(2) Whether or not the state that the intake pressure Pm is below a predetermined fixed pressure and the engine speed Ne is below a predetermined fixed speed continues for a fixed predetermined interval.

(3) Whether or not the electric power supplied to the heater is above a predetermined fixed power.

When the determination at step 333 is affirmative, that is, the storing condition is established, this routine is terminated after the stored resistance BRH is replaced with Rh which is calculated at step 32 of the first heater control routine at step 334.

Note, when the determination at step 333 is negative, this routine is directly terminated without replacing of the stored resistance BRH.

Figure 5:
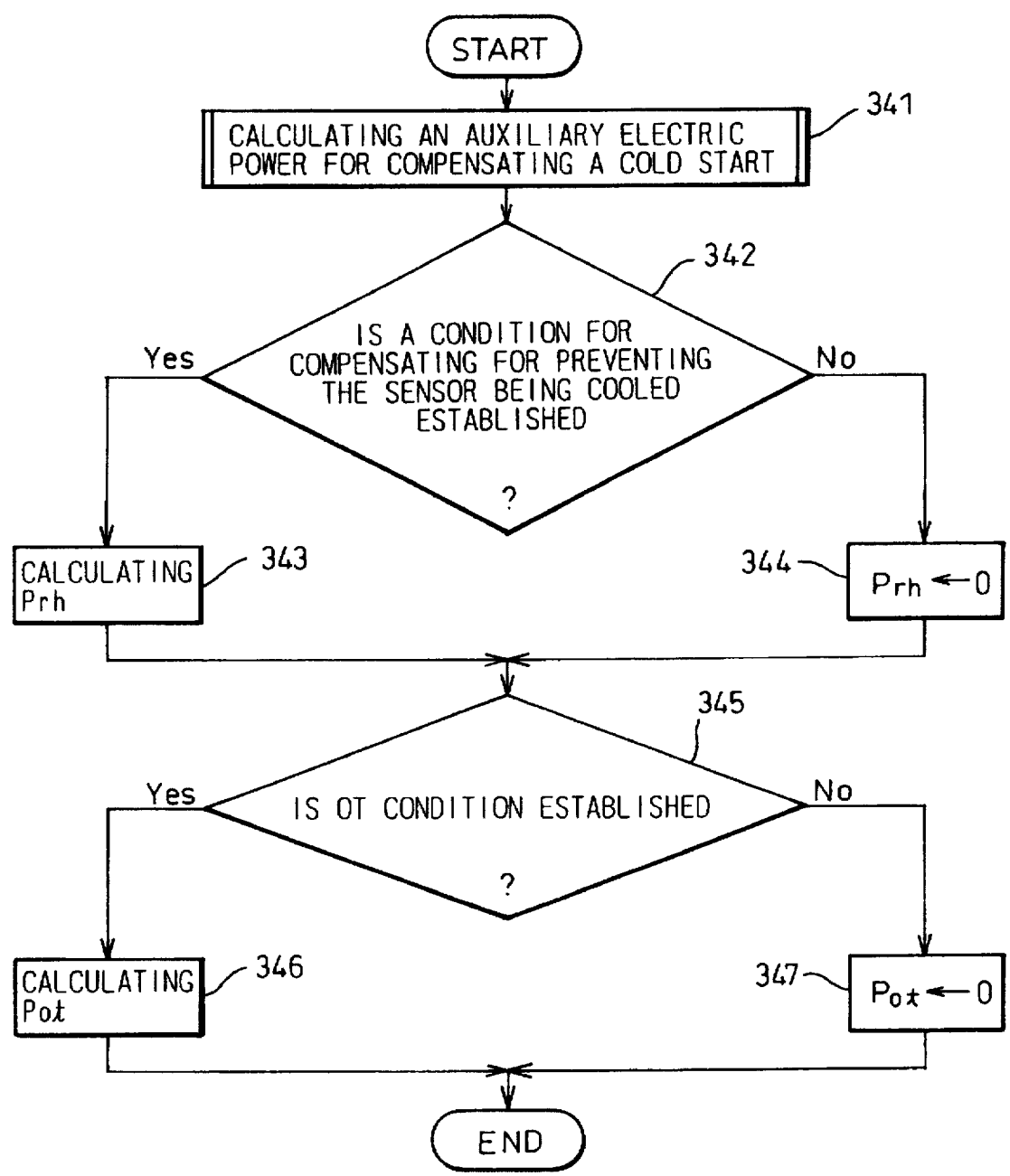
FIG. 5 is a flow chart of an auxiliary electric power determining routine.

FIG. 5 is a flow chart of an auxiliary electric power calculating routine executed at step 34, where an auxiliary electric power for a cold start Pcold is calculated at step 341.

At step 342, it is determined whether or not a condition for compensating for preventing the sensor being cooled at a start of the engine is established.

This compensation prevents the detecting element 111 of the sensor being cooled at a start of the engine by decreasing a basic electric power because the engine speed Ne and the intake pressure Pm are increased at a start from an idling state (that is, an automobile is parked while the engine is running). An electric power is increased for a predetermined fixed interval (for example, three minutes) after the automobile starts running above zero Km/h from a parking state while the engine is running.

When the determination at step 342 is affirmative, that is, when the condition is established, the control proceeds to step 345 after an auxiliary electric power Prh for compensating for preventing the sensor being cooled at a start of the engine is calculated at step 343.

Figure 6:
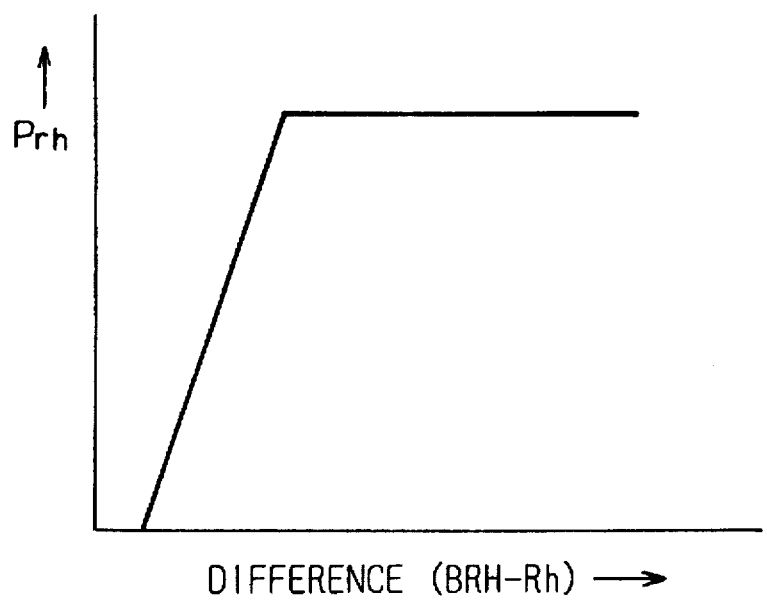
FIG. 6 is a graph to determine an auxiliary electric power for compensating for a start of the engine.

FIG. 6 is a graph to determine the auxiliary electric power Prh, and the ordinate denotes the auxiliary electric power Prh and the abscissa denotes a resistance difference (BRH–Rh) between the stored heater resistance BRH and the current resistance Rh of the heater.

The larger the resistance difference (BRH–Rh) becomes, the larger the auxiliary electric power Prh becomes, but the auxiliary electric power Prh is limited to less than a fixed electric power.

Note, when the determination at step 342 is negative, the control proceeds to step 345 after the auxiliary electric power Prh is set to "0" at step 344.

At step 345, it is determined whether or not a condition for compensating for an over-temperature condition is established.

When the determination at step 345 is affirmative, that is, when the condition for compensating for an over-temperature state is established, this routine is terminated after an auxiliary electric power Pot for compensating an over temperature condition is calculated at step 346.

The auxiliary electric power Pot is used for decreasing a basic electric power to prevent a temperature of the heater rising excessively because it is unavoidable that the temperature of the heater rises excessively when an uncompensated basic electric power is supplied to the heater because the temperature of the exhaust gas rises just after the automobile has been operated at high speed.

Figure 7:
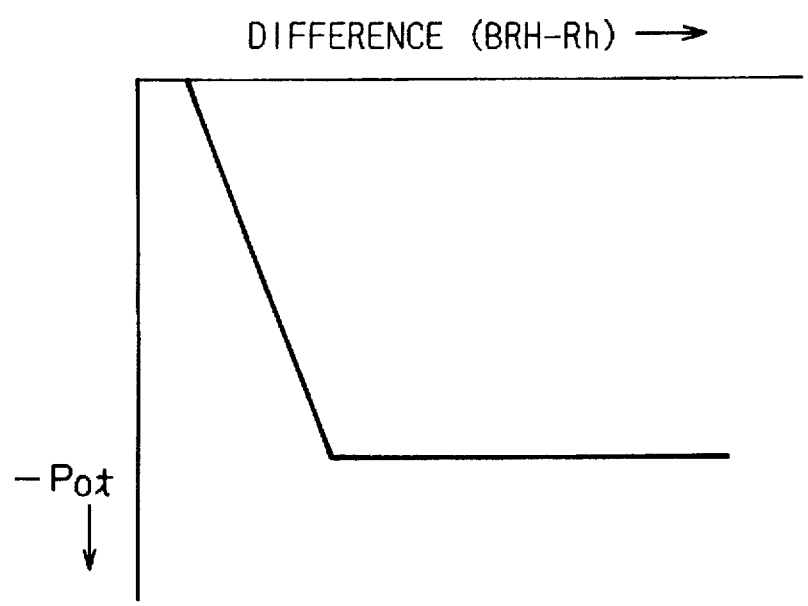
FIG. 7 is a graph to determine an auxiliary electric power for compensating for an over temperature condition.

FIG. 7 is a graph to determine the auxiliary electric power Pot for compensating for the over temperature condition, and the ordinate denotes the auxiliary electric power Pot and the abscissa denotes the resistance difference (BRH–Rh) between the stored heater resistance BRH and the heater resistance Rh.

That is, the larger the resistance difference (BRH–Rh) becomes, the larger the auxiliary electric power Pot becomes, and the auxiliary electric power Pot is limited to less than a fixed electric power.

Note, when the determination at step 345 is negative, this routine is terminated after the auxiliary electric power Pot is set to "0" at step 347.

Figure 8:
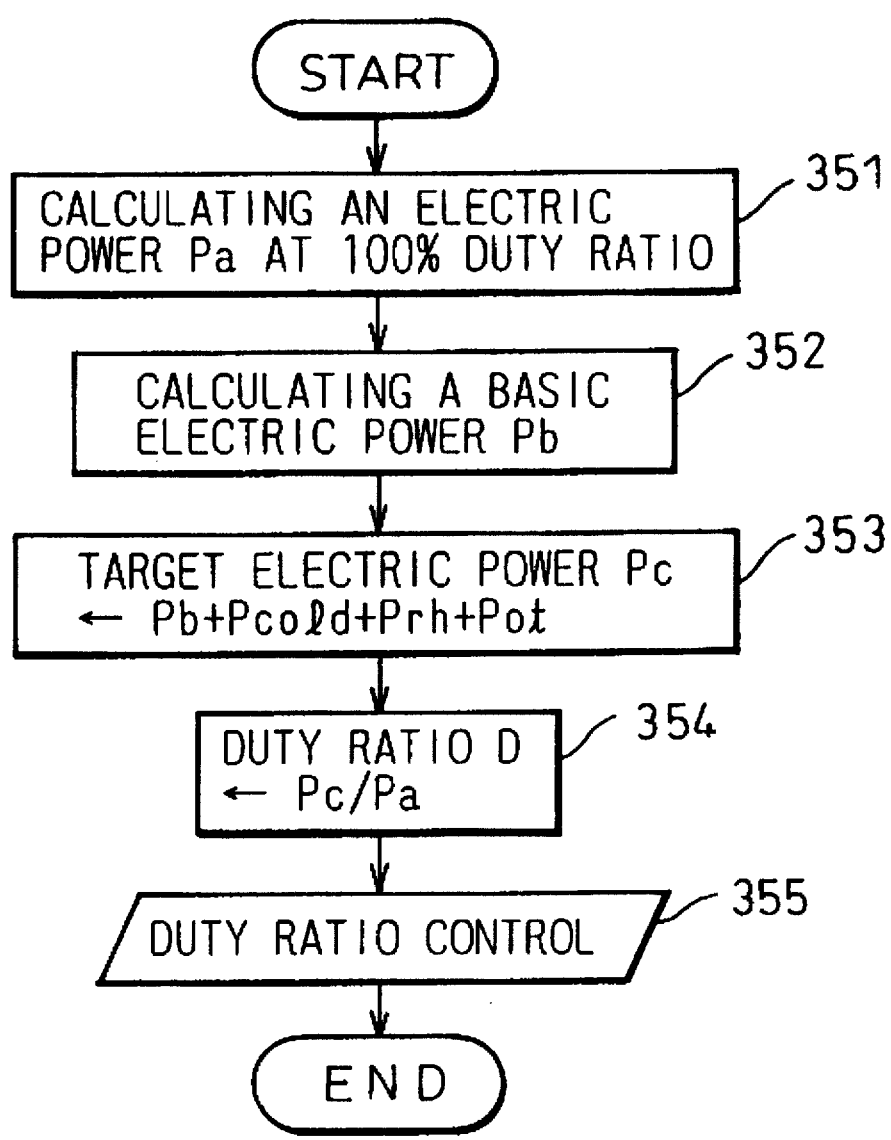
FIG. 8 is a flow chart of a calorific power control routine.

FIG. 8 is a flow chart of a calorific power control routine executed at step 35, and an electric power Pa continuously supplied to the heater for a predetermined fixed interval (for example, 100 msec), that is, an electric power at 100% duty ratio, is calculated based on the voltage Vh supplied to the heater and the current Ih flowing through the heater fetched at step 31 of the first heater control routine.

At step 352, a basic electric power Pb required to maintain the temperature of the detecting element 111 at a predetermined fixed temperature under a current operating condition is calculated as a function of the engine speed Ne and the intake pressure Pm using the map previously stored in the memory 135.

$$Pb \leftarrow Pb(Ne, Pm)$$

Figure 9:
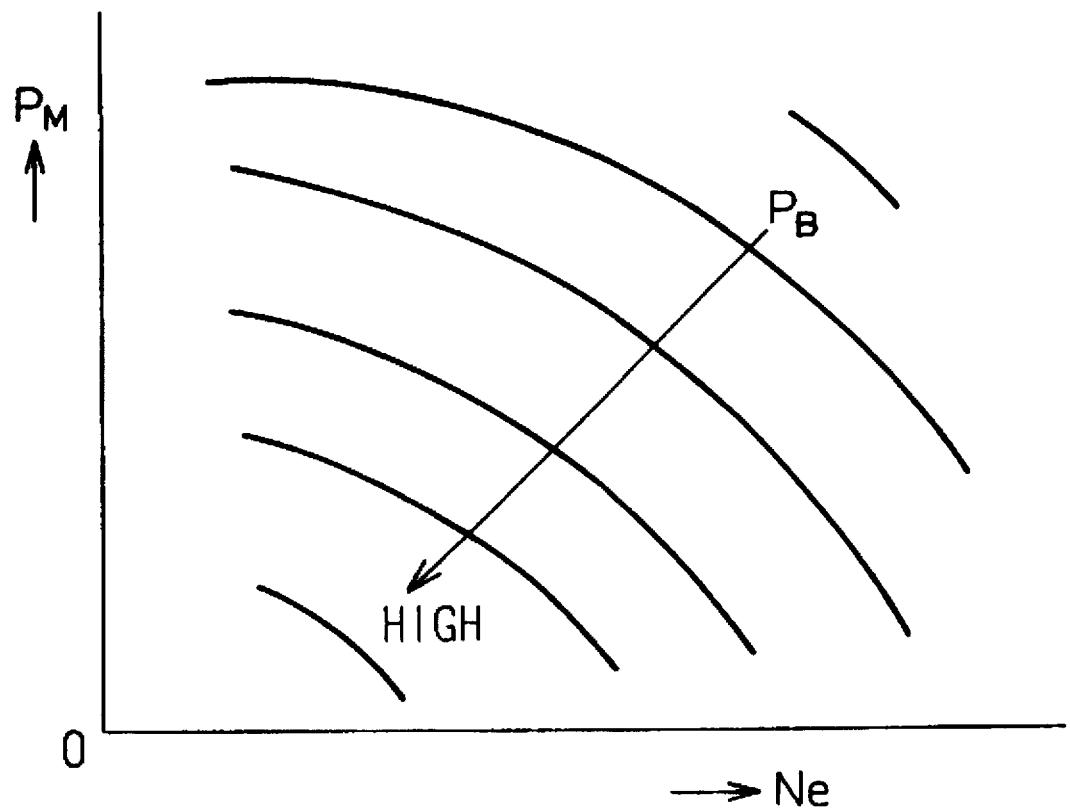
FIG. 9 is a graph to determine a basic electric power.

FIG. 9 is a graph to determine the basic electric power Pb, and the ordinate denotes the intake pressure Pm and the abscissa denotes the engine speed Ne. Note, the parameter is the basic electric power Pb which becomes larger as the intake pressure Pm and the engine speed Ne become smaller, that is, as the quantity of the exhaust gas becomes less and its temperature becomes lower.

At step 353, a target electric power Pc is calculated by adding all auxiliary electric powers to the basic electric power Pb.

$$Pc \leftarrow Pb + Pcold + Prh + Pot$$

At step 354, a duty ratio D is calculated as a ratio of the target electric power to the electric power at 100% duty ratio.

$$D \leftarrow Pc/Pb$$

At step 355, the electric power Pc is supplied to the heater 112 by switching the switching element 122 at the duty ratio D.

Figures 10, 11:
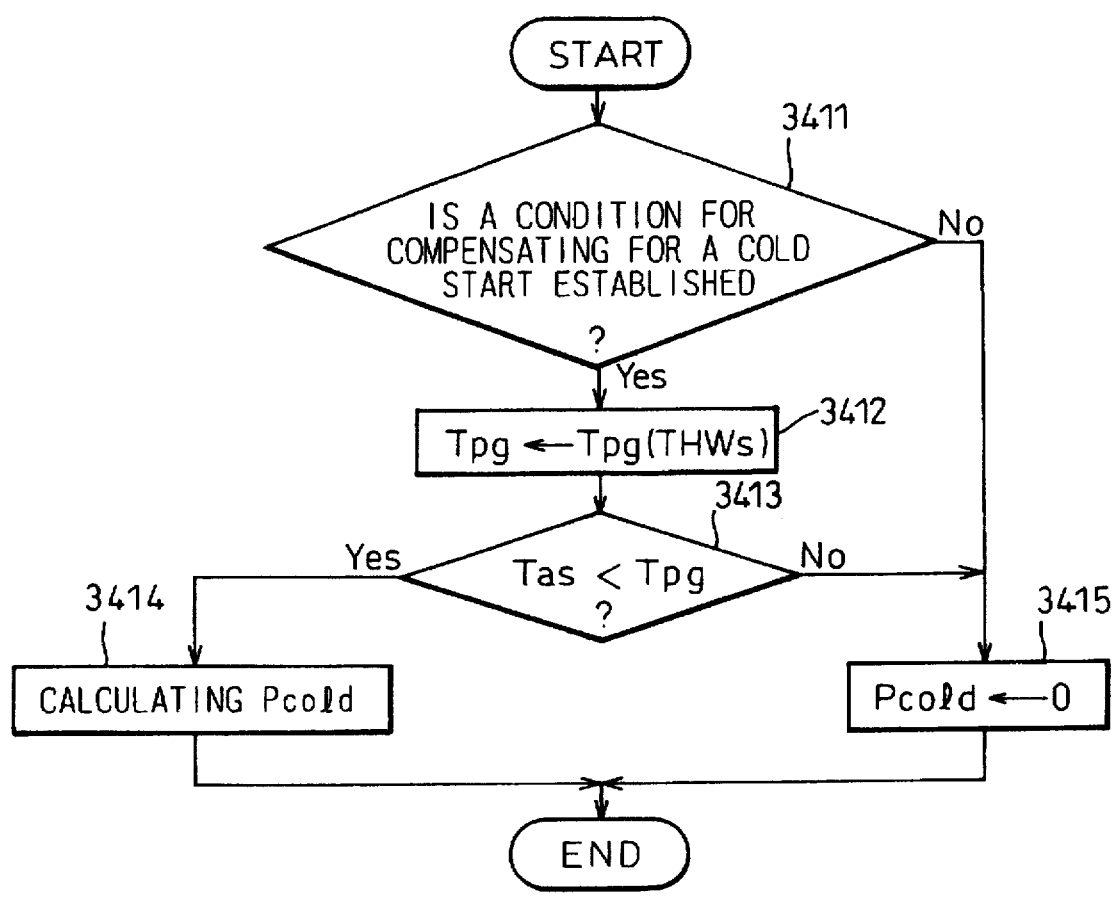
FIG. 10 is a flow chart of a first auxiliary electric power for compensating for a start of the engine determining routine.
FIG. 11 is a first graph to determine a limited interval.

FIG. 10 is a flow chart of a first auxiliary electric power for a cold start determining routine executed at step 341, which determines whether or not a condition for compensating for a cold start at step 3411 exists.

An auxiliary electric power for compensating for a cold start is used to increase the basic electric power during a limited interval Tpg after a cold start of the engine in order to increase the activity of the sensor because a calorific power generated by the basic electric power is not enough to activate the sensor quickly at a cold start.

When the determination at step 3411 is affirmative, the control proceeds to step 3412 where the limited interval Tpg is calculated as a function of the coolant temperature THWs at a start of the engine.

$$Tpg \leftarrow Tpg(THWs)$$

FIG. 11 is a first map to determine the limited interval Tpg, and the limited interval Tpg is stored corresponding to the coolant temperature THWs at a start of the engine in the memory 133. That is, the lower the coolant temperature THWs becomes, the longer the limited interval Tpg is set, because the lower an ambient temperature around the sensor is, the longer an interval to reach an allowable upper limit temperature becomes. Note, the limited interval Tpg is determined so that a temperature of a heater with a low resistance never exceeds an allowable upper limit temperature.

At step 3413, it is determined whether or not an elapsed time Tas after a start of the engine is shorter than the limited interval Tpg.

When the determination at step 3413 is affirmative, that is, when the elapsed time Tas after a start of the engine is shorter than the limited interval Tpg, the routine is terminated after the auxiliary electric power Pcold for compensating for a cold start is determined at step 3414.

Figure 12:
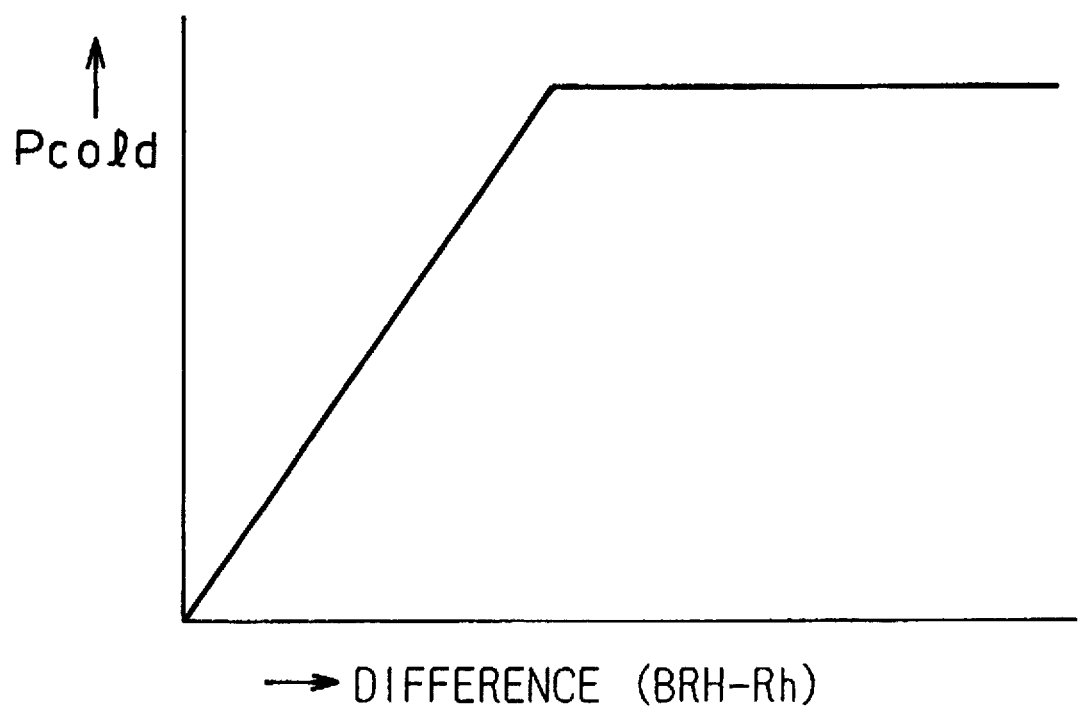
FIG. 12 is a graph to determine an auxiliary electric power for compensating for a cold start of the engine.

FIG. 12 is a graph to determine the auxiliary electric power Pcold for compensating for a cold start, and the ordinate denotes the auxiliary electric power Pcold and the abscissa denotes the resistance difference (BRH–Rh) between the stored heater resistance BRH and the heater resistance Rh.

That is, the larger the resistance difference (BRH–Rh) becomes, the larger the auxiliary electric power Pcold becomes, and the auxiliary electric power Pcold is limited to less than a fixed electric power.

When the determination at step 3411 is negative, that is, when the condition for compensating for a cold start is not established, or when the determination at step 3414 is negative, that is, when the elapsed time Tas is longer than the limited interval Tpg, this routine is terminated after the auxiliary electric power Pcold for compensating for a cold start is set to zero at step 3415.

Figures 13, 14:
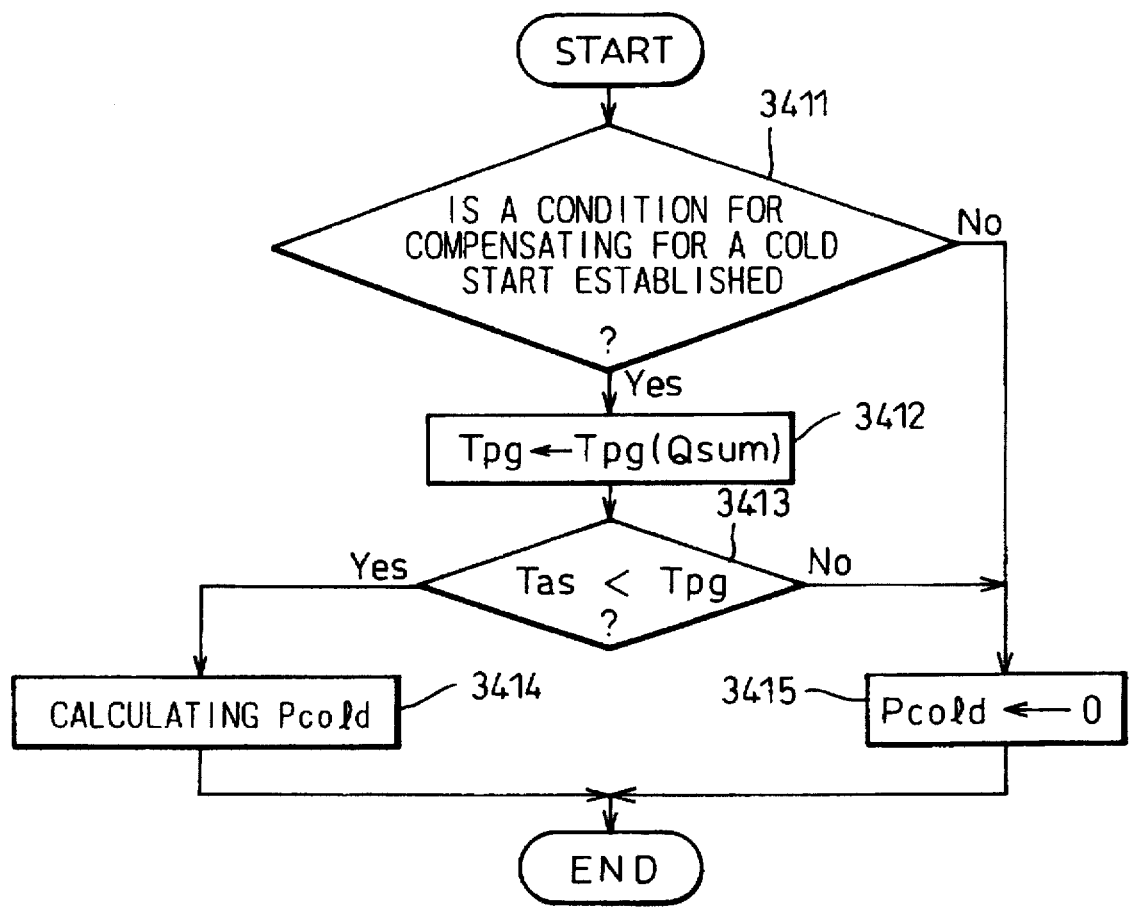
FIG. 13 is a flow chart of a second auxiliary electric power for compensating for a start of the engine determining routine.
FIG. 14 is a second graph to determine a limited interval.

FIG. 13 is a flow chart of a second auxiliary electric power for compensating for a cold start determining routine executed at step 341, and a calculating method of the limited interval Tpg is different from the first auxiliary electric power for compensating for a cold start determining routine.

That is, the limited interval Tpg is determined as the function of an integrated valve opening time or an integrated air-flow rate Qsum after a start of the engine.

$$Tpg \leftarrow Tpg(Qsum)$$

FIG. 14 is a second map to determine the limited interval Tpg, and the limited interval Tpg corresponding to the integrated valve opening time Qsum after a start of the engine is stored in the memory 133. That is, the smaller the integrated valve opening time Qsum becomes, the longer the limited interval Tpg becomes, because the less the calorific power received from exhaust gas becomes, the longer an interval to reach an allowable upper limit temperature becomes. Note, the limited interval Tpg is determined so that a temperature of a heater with a low resistance never exceeds an allowable upper limit temperature.

Figure 15:
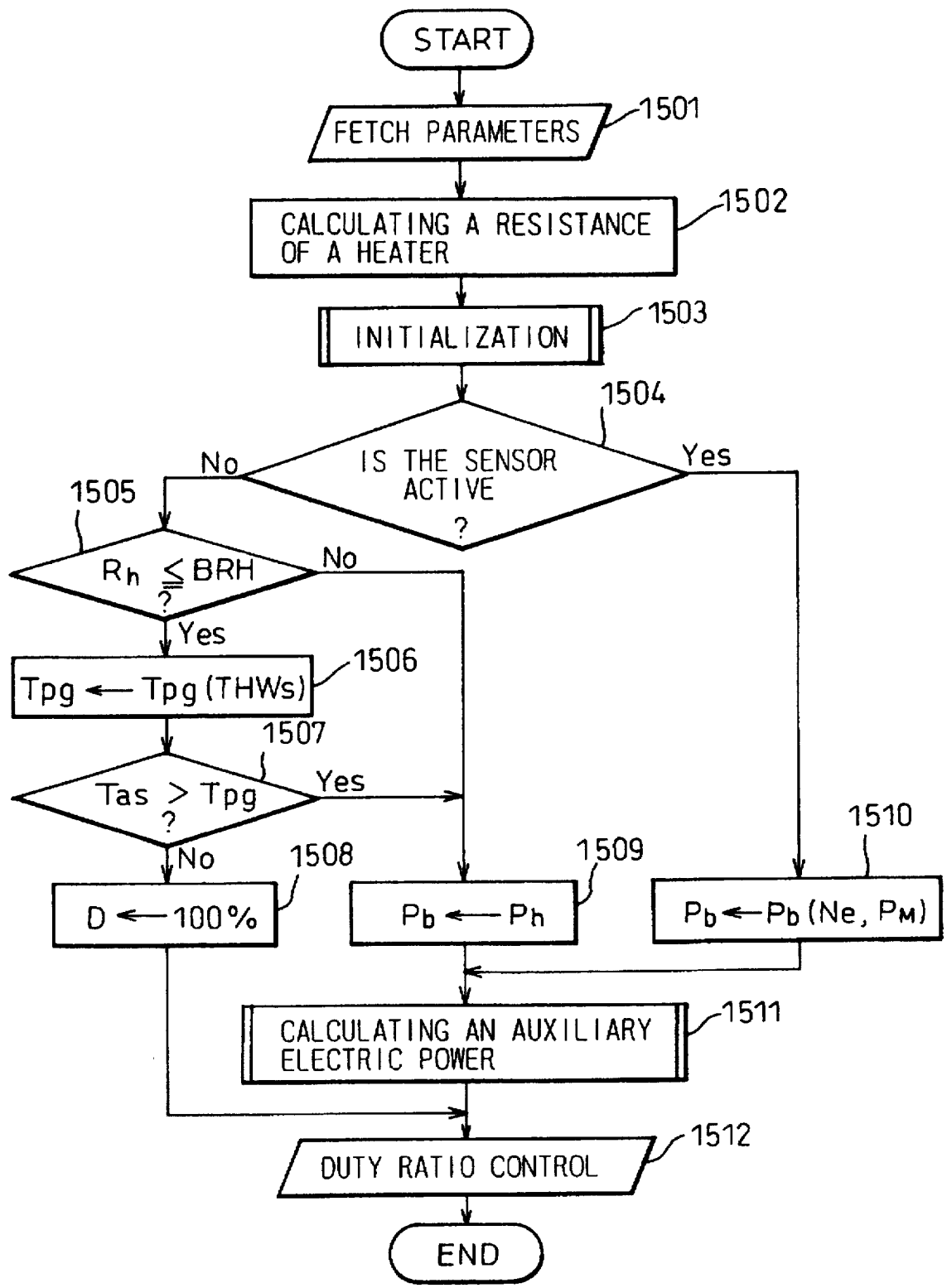
FIG. 15 is a flow chart of a second heater control routine.

FIG. 15 is a flow chart of a second heater control routine executed in the controller 13, and an engine speed Ne, an intake vacuum Pm, a coolant temperature THW, a voltage Vh supplied to the heater, and a current Ih flowing through the heater are fetched at step 1501.

At step 1502, a resistance Rh of the heater is calculated based on the voltage supplied to the heater Vh and the current Ih flowing through the heater by using a following equation.

$$Rh \leftarrow Vh/Ih$$

Then an initializing routine the same as the first heater control routine is executed at step 1503.

At step 1504, it is determined whether or not the sensor 11 is active. For example, the activity of the sensor 11 can be confirmed by determining whether or not an output of the sensor goes above a predetermined level in a fuel-cut condition.

When the determination at step 1504 is negative, that is, when the sensor 11 is not active, the control proceeds to step 1505 where it is determined whether or not the heater resistance Rh calculated at step 1502 is smaller than a predetermined upper limit resistance (for example, the stored resistance BRH).

When the determination at step 1505 is affirmative, the control proceeds to step 1506 where the limited interval Tpg is calculated as a function of a coolant temperature at a start of the engine. Note, this process is the same as the step 3412 of FIG. 10. Therefore, the limited interval Tpg may be determined as the function of an integrated valve opening time or an integrated air-flow rate Qsum after a start of the engine the same as at step 3412 of FIG. 13.

It is determined whether or not an elapsed time Tpg after a start of the engine is longer than the limited interval Tpg at step 1507. When its determination is negative, the control proceeds to step 1512 after the duty ratio is set to 100% to accelerate an activity of the sensor at step 1508.

When the determination at step 1505 is negative, or when the determination at step 1507 is affirmative, the control proceeds to step 1511 after the basic electric power Pb is determined as a predetermined electric power Ph required to maintain the temperature of the heater with a standard resistance at an allowable upper limit temperature (for example, 1100° C.) at step 1509.

When the determination at step 1504 is affirmative, that is, when it is determined that the sensor is active, the control proceeds to step 1511 after the basic electric power Pb is determined as the engine speed Ne and the intake vacuum Pm at step 1510.

$$Pb \leftarrow Pb(Ne, Pm)$$

After a second auxiliary electric power calculating routine is executed at step 1511, the control proceeds to step 1512 where the switching element 122 is switched with the duty ratio D determined at step 1508 or step 1511.

Figure 16:
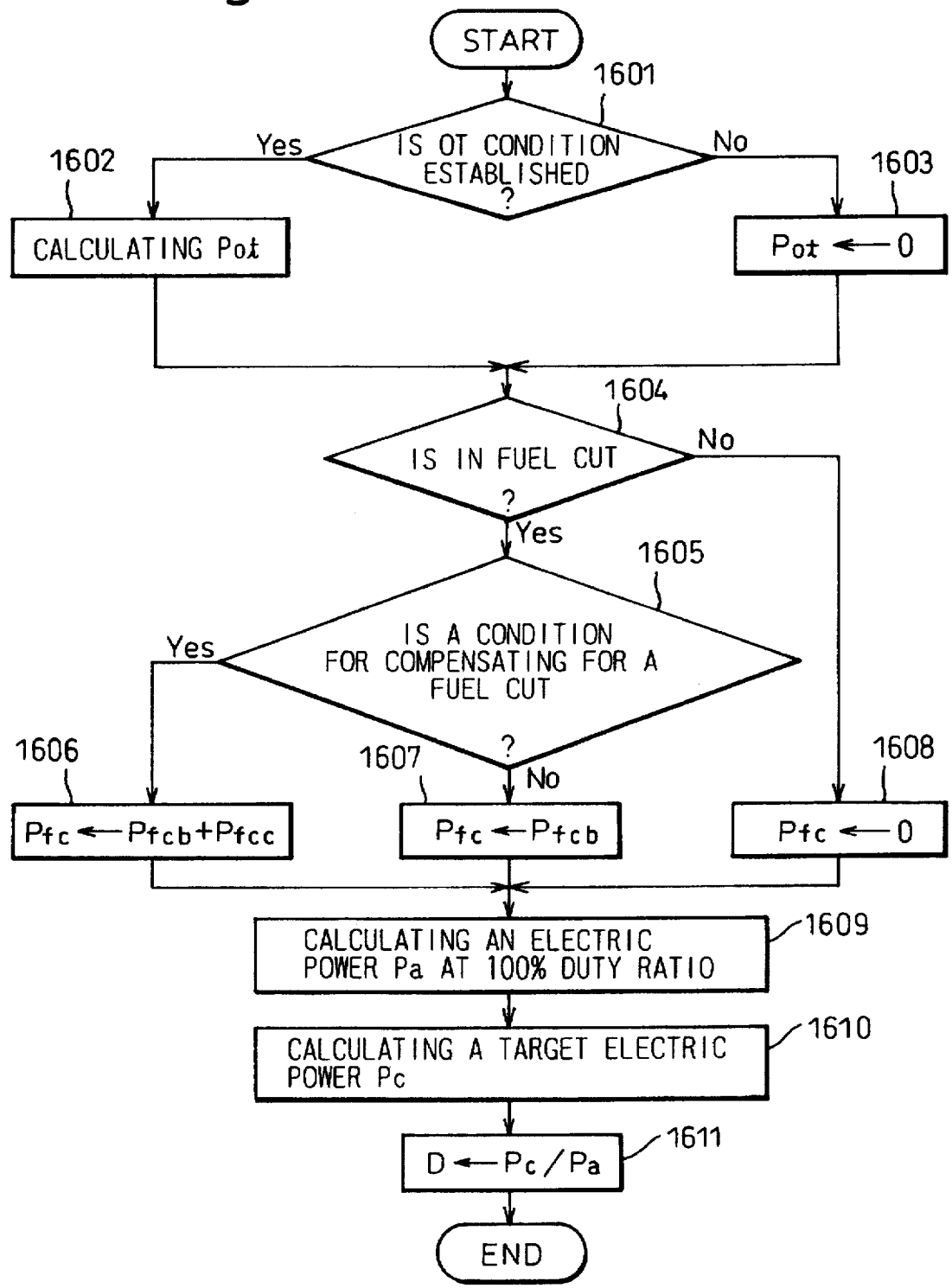
FIG. 16 is a flow chart of a second auxiliary electric power determining routine.

FIG. 16 is a flow chart of a second auxiliary electric power calculating routine executed at step 1511, and it is determined whether or not a condition for compensating for an over temperature condition is established at step 1601.

When the determination at step 1601 is affirmative, the control proceeds to step 1604 after the auxiliary electric power Pot for compensating for an over temperature condition is calculated at step 1602.

When the determination at step 1601 is negative, the control proceeds to step 1604 after the auxiliary electric power Pot for compensating for an over temperature condition is set to zero at step 1603.

It is determined whether or not the engine is operating under the fuel-cut state at step 1604. When the engine is operating under the fuel-cut state, it is determined whether or not a condition for compensating for the fuel-cut state is established at step 1605.

When the determination at step 1605 is affirmative, the control proceeds to step 1609 after an auxiliary electric power Pfc is calculated as a sum of a fundamental electric power Pfcf during the fuel-cut state and an additional electric power Pfca during the fuel-cut state at step 1606.

When the determination at step 1605 is negative, the control proceeds to step 1609 after the auxiliary electric power Pfc is determined as an fundamental electric power Pfcf during the fuel-cut state at step 1607.

When the determination at step 1604 is negative, the control proceeds to step 1609 after the auxiliary electric power Pfc is set to zero at step 1608.

At step 1609, an electric power Pa continuously supplied to the heater for a predetermined fixed interval (for example, 100 msec), that is, an electric power at 100% duty ratio is calculated based on the voltage Vh supplied to the heater and the current Ih flowing through the heater.

At step 1610, a target electric power Pc is calculated by adding all auxiliary electric powers to the basic electric power Pb.

$$Pc \leftarrow Pb+Pot+Pfc$$

This routine is terminated after a duty ratio D is calculated as a ratio of the target electric power to the electric power at 100% duty ratio at step 1611.

$$D \leftarrow Pc/Pb$$

According to the second heater control routine, the activity of the sensor can be accelerated because an electric power required to maintain the temperature of the sensor at the allowable upper limit temperature is supplied after supplying the electric power at 100% duty ratio to the heater. Further according to this routine, when a failed heater is replaced with a new heater which has a lower resistance than the failed heater, an excessive temperature rising and/or a break-down of the new heater can be prevented.

I claim:

1. A heater controller to control an electric power supplied to a heater for heating an air-fuel ratio sensor which detects an air-fuel ratio of an internal combustion engine, comprising:

an engine condition detecting means for detecting an operating condition of the engine;

a resistance determining means for determining a resistance of the heater;

a storing means for storing the resistance determined by said resistance determining means as a stored resistance when it is determined that the temperature of the heater is stable based on the operating condition of the engine determined by said engine condition detecting means;

an electric power increasing means for increasing an electric power supplied to the heater in accordance with a current resistance of the heater determined by said resistance determining means and the stored resistance stored in said storing means during a warm up of the sensor after a start of the engine; and a limiting means for limiting an interval for supplying the electric power increased by said electric power increasing means within a predetermined fixed interval so that the temperature of the heater does not exceed a fixed upper limit temperature in spite of a variation in the heater.

2. A heater controller of claim 1, further comprising an ambient temperature estimating means for estimating an ambient temperature around the sensor; and said limiting means determines a limiting interval in accordance with an estimated ambient temperature estimated by said ambient temperature estimating means.

3. A heater controller of claim 1, further comprising an airflow rate integrating means for integrating an air-flow rate after a starting of the engine; and said limiting means determines a limiting interval in accordance with an integrated air flow rate integrated by said air-flow integrating means.

4. A heater controller of claim 1, further comprising a fuel-flow rate integrating means for integrating a fuel-flow rate injected from at least one injection valve after a starting of the engine; and said limiting means determines a limiting interval in accordance with an integrated fuel-flow rate integrated by said fuel-flow rate integrating means.

5. A heater controller of claim 1, wherein said electric power increasing means increases an electric power by adding an auxiliary electric power determined in accordance with a current resistance of the heater determined by said resistance determining means and the stored resistance stored in said storing means to a basic electric power determined in accordance with the engine operating condition detected by said engine condition detecting means.

6. A heater controller of claim 1, wherein said electric power increasing means supplies an electric power continuously to the heater when a current resistance of the heater determined by said resistance determining means is below a predetermined upper limit resistance, while an electric power is increased in accordance with a current resistance of the heater determined by said resistance determining means and the stored resistance stored in said storing means when a current resistance of the heater determined by said resistance determining means is above a predetermined upper limit resistance.

7. A heater controller of claim 6, further comprising an ambient temperature estimating means for estimating an ambient temperature around the sensor; and said limiting means determines a limiting interval in accordance with an estimated ambient temperature estimated by said ambient temperature estimating means.

8. A heater controller of claim 6, further comprising an air-flow rate integrating means for integrating an air-flow rate after a starting of the engine; and said limiting means determines a limiting interval in accordance with an integrated air flow rate integrated by said air-flow integrating means.

9. A heater controller of claim 6, further comprising a fuel-flow rate integrating means for integrating a fuel-flow rate injected from at least one injection valve after a starting of the engine; and said limiting means determines a limiting interval in accordance with an integrated fuel-flow rate integrated by said fuel-flow rate integrating means.

10. A heater control method to control an electric power supplied to a heater for heating an air-fuel ratio sensor which detects an air-fuel ratio of an internal combustion engine, comprising the steps of:

determining an operating condition of the engine;

detecting a resistance of the heater;

storing the resistance detected at said resistance detecting step as a stored resistance when it is determined that the temperature of the heater is stable based on the operating condition of the engine determined at said operating condition determining step;

increasing an electric power supplied to the heater in accordance with a current heater resistance detected at said resistance detecting step and the stored resistance stored at said storing step during warming up of the air-fuel ratio sensor after a starting of the engine; and limiting an interval for increasing the electric power at said electric power increasing step within a predetermined fixed interval so that the temperature of the heater does not exceed a fixed upper limit temperature in spite of a variation in the heater.

11. A heater control method of claim 10, further comprising a step of estimating an ambient temperature around the air-fuel ratio sensor; and said limiting step is to determine a limiting interval in accordance with an estimated ambient temperature estimated at said ambient temperature estimating step.

12. A heater control method of claim 10, further comprising a step of integrating an air-flow rate after a starting of the engine; and said limiting step is to determine a limiting interval in accordance with an integrated air flow rate integrated at said air-flow integrating step.

13. A heater control method of claim 10, further comprising a step of integrating a fuel-flow rate injected from injection valves after a starting of the engine; and said limiting step is to determine a limiting interval in accordance with an integrated fuel-flow rate integrated at said fuel-flow rate integrating step.

14. A heater control method of claim 10, wherein, at said electric power increasing step, an electric power is increased by adding an auxiliary electric power determined in accordance with a current resistance of the heater determined at said resistance determining step and the stored resistance stored at said storing step to a basic electric power determined in accordance with the engine operating condition detected at said engine condition detecting step.

15. A heater control method of claim 10, wherein, at said electric power increasing step, an electric power is continuously supplied to the heater when a current resistance of the heater determined at said resistance determining step is below a predetermined upper limit resistance, while an electric power is increased in accordance with a current resistance of the heater determined at said resistance determining step and the stored resistance stored at said storing step when a current resistance of the heater determined at said resistance determining step is above a predetermined upper limit resistance.

16. A heater control method of claim 15, further comprising an ambient temperature estimating step for estimating an ambient temperature around the sensor; and said limiting step determines a limiting interval in accordance with an estimated ambient temperature estimated at said ambient temperature estimating step.

17. A heater control method of claim 15, further comprising an air-flow rate integrating step for integrating an air-flow rate after a starting of the engine; and said limiting step determines a limiting interval in accordance with an integrated air flow rate integrated at said air-flow integrating step.

18. A heater control method of claim 15, further comprising a fuel-flow rate integrating step for integrating a fuel-flow rate injected from at least one injection valve after a starting of the engine; and said limiting step determines a limiting interval in accordance with an integrated fuel-flow rate integrated at said fuel-flow rate integrating step.

\* \* \* \* \*